(12) United States Patent
Kohler

(10) Patent No.: US 10,010,727 B2
(45) Date of Patent: Jul. 3, 2018

(54) ENERGY DEPOSITION ZONE DETERMINATION FOR A CATHETER WITH AN ULTRASOUND ARRAY

(71) Applicant: Profound Medical Inc., Mississauga (CA)

(72) Inventor: Max Oskar Kohler, Eindhoven (NL)

(73) Assignee: Profound Medical Inc., Mississauga, ON (CA)

( * ) Notice: Subject to any disclaimer, the term of this patent is extended or adjusted under 35 U.S.C. 154(b) by 316 days.

(21) Appl. No.: 14/781,598

(22) PCT Filed: Apr. 4, 2014

(86) PCT No.: PCT/EP2014/056831
§ 371 (c)(1),
(2) Date: Oct. 1, 2015

(87) PCT Pub. No.: WO2014/170144
PCT Pub. Date: Oct. 23, 2014

(65) Prior Publication Data
US 2016/0045771 A1 Feb. 18, 2016

(30) Foreign Application Priority Data
Apr. 5, 2013 (EP) .................................... 13162504

(51) Int. Cl.
*A61N 7/02* (2006.01)
*A61B 5/055* (2006.01)
(Continued)

(52) U.S. Cl.
CPC .............. *A61N 7/022* (2013.01); *A61B 5/055* (2013.01); *A61B 8/12* (2013.01);
(Continued)

(58) Field of Classification Search
CPC ..... A61B 2090/374; A61B 5/055; A61B 8/12; A61N 2007/0078; A61N 2007/0095; A61N 7/022
See application file for complete search history.

(56) References Cited

U.S. PATENT DOCUMENTS

| 6,188,923 | B1 * | 2/2001 | Bechtold | ................ | A61N 7/022 |
| | | | | | 600/412 |
| 6,618,620 | B1 * | 9/2003 | Freundlich | ............... | A61N 7/02 |
| | | | | | 600/437 |

(Continued)

FOREIGN PATENT DOCUMENTS

| JP | 2006523116 A | 10/2006 |
| JP | 2009247641 A | 10/2009 |

(Continued)

OTHER PUBLICATIONS

Kinsey et al "Interstitial Ultrasound Applicators With Dynamic Angular Control for Thermal Ablation of Tumors Under MR Guidance" Proceedings of the 26 Annual International Conference on the IEEE EMBS, Sep. 1-5, 2004, p. 2496-2499.

(Continued)

*Primary Examiner* — Michael Peffley
(74) *Attorney, Agent, or Firm* — Intrinsic Law Corp.

(57) ABSTRACT

The invention provides for a medical apparatus (300) comprising: a magnetic resonance imaging system (302); an ultrasonic system (322) for connecting to a catheter (324, 504, 600) with an ultrasound array (400, 402, 404, 508, 602, 604). The ultrasonic system is operable for driving the ultrasound array. Machine executable instructions (354, 356, 358) cause a processor (334) for controlling the medical apparatus to: generate (100, 202) at least one acoustic radiation impulse with the ultrasonic system, wherein the generated ultrasound energy is below a predetermined level; acquire (102, 204) the magnetic resonance data using an (Continued)

acoustic radiation force imaging pulse sequence; reconstruct (104, 206) at least one acoustic radiation force pulse image using the magnetic resonance data; and determine (106, 208) an energy deposition zone for the catheter using at least partially the at least one acoustic radiation force pulse image.

13 Claims, 7 Drawing Sheets

(51) Int. Cl.
  *A61B 8/12* (2006.01)
  *A61N 7/00* (2006.01)
  *A61B 90/00* (2016.01)

(52) U.S. Cl.
  CPC . *A61B 2090/374* (2016.02); *A61N 2007/0078* (2013.01); *A61N 2007/0095* (2013.01)

(56) References Cited

U.S. PATENT DOCUMENTS

| | | | |
|---|---|---|---|
| 8,661,873 B2* | 3/2014 | Medan | A61B 8/587 73/1.82 |
| 9,177,543 B2* | 11/2015 | Vitek | A61N 7/02 |
| 9,579,042 B2* | 2/2017 | Zur | A61N 7/02 |
| 2008/0097207 A1 | 4/2008 | Cai | |
| 2010/0191113 A1 | 7/2010 | Hazard et al. | |
| 2011/0270136 A1 | 11/2011 | Vitek | |
| 2012/0065492 A1 | 3/2012 | Gertner | |

FOREIGN PATENT DOCUMENTS

| | | |
|---|---|---|
| JP | 2010515472 A | 5/2010 |
| JP | 2012528649 A | 11/2012 |
| WO | 2008143998 A1 | 11/2008 |
| WO | WO2011135458 A2 | 11/2011 |
| WO | WO2012066417 A1 | 5/2012 |
| WO | 2013055795 A1 | 4/2013 |
| WO | WO2013046074 A1 | 4/2013 |
| WO | 2013153509 A1 | 10/2013 |

OTHER PUBLICATIONS

Ross et al, "Highly Directional Transurethral Ultrasound Applications With Rotational Control . . " Physics in Med. and Bio. 49, (2004) p. 189-204.

Larrat et al "MR Guided Adaptive Focusing of Ultrasound" IEEE Transactions on Ultrasonics, Ferroelectrics and Frequency Coltrol. Vo. 57, No. 8 AUT. 2010 p. 1734-1747.

Sarvazyan et al, "Shear Wave Elasticity Imaging: A New Ultrasonic . . " Ultrasound in Med. and Biol. vol. 24, No. 9, p. 1419-1435 (1998).

Hertzberg et al "Ultrasound Focusing Using Magnetic Resonance Acoustic Radiation Force Imaging . . " Med. Phys. 37 (6) Jun. 2010. p. 2934-2942.

Holbrook et al "In Vivo MR Acoustic Radiation Force Imaging in the Porcine Liver" Med. Phys. 38, (9) p. 5081-5089 (Sep. 2011).

McDannold et al "Magnetic Resonance Acoustic Radiation Force Imaging" Med. Phys. 35 (8) Aug. 2008 p. 3748-3758.

* cited by examiner

ENERGY DEPOSITION ZONE DETERMINATION FOR A CATHETER WITH AN ULTRASOUND ARRAY

CROSS REFERENCE TO RELATED APPLICATIONS

This application is a U.S. national phase application of International Application No. PCT/EP2014/056831, filed on Apr. 4, 2014, which claims the benefit of EP 13162504.8 filed on Apr. 5, 2013 and is incorporated herein by reference.

TECHNICAL FIELD OF THE INVENTION

The invention relates to the deposition of ultrasonic energy into a subject using a catheter, in particular the guidance of the catheter using acoustic radiation force imaging.

BACKGROUND OF THE INVENTION

Non or minimally invasive treatment of prostate tumors is a field of increasing interest. High-intensity focused ultrasound (HIFU) therapy of prostate tumors has shown great promise in reducing the side effects of well-established treatments, while still treating the tumor effectively. Most of the clinical cases performed to date have been under ultrasound guidance, but MR guidance holds several benefits that may further improve the clinical outcome of the procedures. In addition to temperature imaging, MR guidance also allows for using MRI for planning of the procedure.

Magnetic resonance acoustic radiation force imaging is a Magnetic Resonance technique which is able to map displacements produced by focused ultrasound pulses. The journal publication McDonnold et al. Med. Phys. 35 (8), August 2008, pages 3748 to 3758 provides a review of magnetic resonance acoustic radiation force imaging and how to apply the technique.

In Holbrook et. al., Med. Phys. 38 (9), September 2011, pages 5081 to 5089 discloses the use of Magnetic Resonance acoustic radiation force imaging to provide a method of visualizing the transducer focus quickly, for High Intensity Focused Ultrasound (HIFU), without damaging tissue to allow accurate execution of a treatment plan.

SUMMARY OF THE INVENTION

The invention provides for a medical apparatus, a method of operating the medical apparatus, and a computer program product in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks. A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

A 'pulse sequence' as used herein encompasses a set of sequential commands used to control a magnetic resonance imaging system in order to perform a particular imaging protocol. An acoustic radiation force imaging pulse sequence is a pulse sequence is a pulse sequence which enables the magnetic resonance imaging system to acquire magnetic resonance data that can be used to produce maps of displacements caused by ultrasound pulses.

A 'capacitive micromachined ultrasonic transducer' (CMUT) as used herein encompasses a capacitive ultrasound transducer that has been manufactured using micromachining technologies. Micromachining technologies are thin film manufacturing techniques; typically they are performed using processes identical to or similar to those used for manufacturing integrated circuits.

Recent developments have led to the prospect that medical ultrasound transducers can be manufactured by semiconductor processes. These processes may be the same ones used to produce the circuitry needed by an ultrasound probe such as a CMOS process. These developments have produced micromachined ultrasonic transducers or MUTs.

MUTs have been fabricated in two design approaches, one using a semiconductor layer with piezoelectric properties (PMUTs) and another using a diaphragm and substrate with electrode plates that exhibit a capacitive effect (CMUTs). The CMUT transducers are tiny diaphragm-like devices with electrodes that convert the sound vibration of a received ultrasound signal into a modulated capacitance. For transmission the capacitive charge applied to the electrodes is modulated to vibrate the diaphragm of the device and thereby transmit a sound wave.

Since these devices are manufactured by semiconductor processes the devices generally have dimensions in the 10-200 micron range, but can range up to device diameters of 300-500 microns. Many such individual CMUTs can be connected together and operated in unison as a single transducer element. For example, four to sixteen CMUTs can be coupled together to function in unison as a single transducer element. A typical two dimensional transducer array currently may have 2000-3000 piezoelectric transducer elements. When fabricated as a CMUT array, over one million CMUT cells may be used. Surprisingly, early results have indicated that the yields, from a semiconductor fabrication plant, of CMUT arrays of this size should be markedly improved over the yields for lead zirconate titanate (PZT) arrays of several thousand transducer elements.

In one aspect the invention provides for a medical apparatus comprising a magnetic resonance imaging system for acquiring magnetic resonance data from a subject. The medical apparatus further comprises an ultrasonic system operable for connecting to a catheter with an ultrasound array. The ultrasonic system is operable for driving the ultrasound array. Driving the ultrasound array as used herein encompasses providing electrical power to the ultrasound array such that it is able to generate ultrasound. The medical apparatus further comprises a memory for storing machine-executable instructions. The medical apparatus further comprises a processor for controlling the medical apparatus. Execution of the machine-executable instructions cause the processor to control the ultrasonic system to generate at least one acoustic radiation impulse by the ultrasonic system at a location of a target zone. The generated ultrasound is below a predetermined level. The predetermined level may be selected such that the generated ultrasonic energy does not cause damage locally in the subject.

For instance the predetermined may be set such that the heating of the subject in the target zone or in the vicinity around the target zone is such that tissue necrosis does not occur. Execution of the machine-executable instructions further cause the processor to acquire the magnetic resonance data by controlling the magnetic resonance imaging system with a pulse sequence at least partially during the generation of the at least one acoustic radiation impulse. The pulse sequence is an acoustic radiation force imaging pulse sequence. Execution of the machine-executable instructions further cause the processor to reconstruct at least one acoustic radiation force pulse image using the magnetic resonance data. Execution of the machine-executable instructions further cause the processor to determine an energy deposition zone for the catheter using at least partially the at least one acoustic radiation force pulse image.

This embodiment may have the benefit that the determination of where the energy deposition will be performed by the catheter can be done very rapidly and very efficiently using acoustic radiation force imaging or also known as acoustic radiation force impulse imaging.

Acoustic radiation force impulse imaging is applied using focused ultrasound pulses using transducer arrays that direct ultrasound to a focus. The images created from the acoustic radiation force imaging are typically stiffness weighted and are used to provide information about local mechanical tissue properties. In this embodiment the similar technique is used, however not with a high intensity focused ultrasound system but with the use of a catheter. By its nature the catheter does not necessarily direct the ultrasound to a focused point. This a challenge is using catheters for ultrasound therapy. Using acoustic radiation force imaging, the overall distribution of where the ultrasound energy will go can be accurately predicted. When a catheter is used the ultrasound energy will not just to a maximum or a focal point, but may be distributed throughout the subject. The acoustic radiation force imaging may enable the essentially unfocused ultrasound from a catheter to be more accurately targeted or directed within a subject. A technique like magnetic resonance thermometry could be used for targeting the ultrasound also, however the tissue would need to be heated a measureable amount. Acoustic radiation force imaging has the advantage over magnetic resonance thermometry in that it gives faster results and only minimal heating occurs.

The determination of the energy deposition zone may be determined for instance by noting where the maximum radiation force produced by the ultrasound is. This may produce more rapid and accurate information than performing say for instance a test pulse. In this embodiment the energy may be much lower than is needed to be detected by say a test pulse. When performing a test pulse a reduced energy may be used and an increase in the temperature may be noted. In the present embodiment the tissue displacement can be caused by a much smaller ultrasound impulse. This may enable more rapid or more frequent testing of the location of the energy deposition zone for the catheter. This may enable more accurate targeting using the catheter than with traditional test pulse protocols.

In another embodiment, the catheter comprises multiple ultrasound elements. Each of the multiple ultrasound elements is operable for producing ultrasound at multiple frequencies. The ultrasonic system is operable for controlling each of the ultrasound elements to generate ultrasound at the multiple frequencies. The at least one acoustic radiation impulse comprises multiple pulses or impulses with ultrasound generated using at least some of the multiple frequencies. Execution of the instructions further causes the processor to reconstruct multiple acoustic radiation force image pulse images using magnetic resonance data acquired at least partially during the multiple pulses.

Execution of the machine-executable instructions further causes the processor to receive a treatment plan descriptive of a target zone within the subject. The energy deposition zone may be determined as a function of the ultrasound frequency generated by the ultrasound elements. Execution of the instructions may further cause the processor to to determine a sonication frequency for each of the ultrasound elements using this frequency dependent energy deposition zone.

Depending upon the construction of the catheter the multiple ultrasound elements may have several or a range of frequencies which it is capable of generating ultrasound at. For instance if piezoelectric elements are used then there may be a discreet number of frequencies which are practical to use. If a so called CMUT capacitive micromachined ultrasonic transducer is used then the frequency may be freely selectable within a range that is determined by the structure of the CMUT transducers. In this embodiment the procedure is repeated using multiple frequencies and then frequencies are chosen for the various ultrasound elements such that the ultrasound is directed to the target zone.

This embodiment may be particularly beneficial because the determination of the energy deposition zone can be made for different frequencies and individual or groups of ultrasound elements using acoustic radiation force imaging. A large number of such images can be constructed very rapidly and without the use of effectively heating the tissue very much. This may enable more refined targeting of the target zone than would be possible if say a conventional test pulse were used with thermal imaging.

In another embodiment the multiple ultrasound elements comprise at least one capacitive micromachined ultrasonic transducer array. The arrays may be operated in a variety of ways. For instance the array may be operated as a single ultrasound element in some embodiments where all of the capacitive micromachined ultrasonic transducers are operated at the same frequency. In other embodiments the frequency may be varied across one CMUT array. In other embodiments the phase produced by the individual capacitive micromachined ultrasonic transducers may also be controlled. This may enable more accurate or more precise targeting using the catheter.

In another embodiment the ultrasound system is operable for adjusting the focus of the at least one capacitive micromachined ultrasonic transducer array by controlling the phase of electrical power supplied to capacitive elements of the at least one capacitive micromachined ultrasonic transducer. Execution of the machine-executable instructions causes the processor to control the phase of the electrical power supplied to capacitive elements of the at least one capacitive micromachined ultrasonic transducer to control the location of the energy deposition zone. In this embodiment controlling the frequency the phase of electrical power is also performed. This may enable a form of targeting of the target zone and reduce the amount that the catheter needs to be manipulated.

In another embodiment the multiple ultrasound elements comprise piezoelectric transducers.

In another embodiment execution of the instructions further causes the processor to control the ultrasonic system to generate ultrasound above the predetermined threshold in the energy deposition zone. For instance once the location of the energy deposition zone is known accurately the catheter may then be used for ablating tissue or for locally heating a portion of the subject.

In another embodiment the ultrasound system is operable for controlling the phase of electrical power supplied to the ultrasound array. Execution of the machine-executable instructions further causes the processor to adjust the phase of the multiple ultrasound transducer elements to modify the location of the energy deposition zone to match the target zone.

In another embodiment execution of the machine-executable instructions further causes the processor to perform a beam path evaluation using the at least one acoustic radiation force pulse image. The beam path as is used herein encompasses a path which the ultrasound takes between the transducer and the energy deposition zone. This embodiment may be beneficial because using the acoustic radiation force imaging the intensity of the ultrasound which will be generated between the transducer and the energy deposition zone can be estimated accurately by the displacement generated. This may be useful in avoiding such effects as near field heating or the burning of the surface of a subject due to high intensity ultrasound in the near field.

In another embodiment execution of the machine-executable instructions further causes the processor to determine a distance between the energy deposition zone and a predetermined volume in the subject. This for instance may be considered to be equivalent as performing a test shot using the system. The energy deposition zone is where the energy during a sonication will likely go and the predetermined volume may be a volume which is desired to be targeted within the subject. Determining the distance between the two may be useful because then a physician or other operator can reposition the catheter or electrical targeting can be changed within the catheter to reduce the distance between the energy deposition zone and the predetermined volume.

In another embodiment the medical apparatus comprises the catheter.

In another embodiment the catheter is a transurethral catheter.

In another embodiment the catheter is an interstitial catheter.

In another embodiment the catheter is an esophageal catheter.

In another aspect the invention provides for a method of operating a medical apparatus. The medical apparatus comprises a magnetic resonance imaging system for acquiring magnetic resonance data from a subject. The medical apparatus further comprises an ultrasonic system operable for connecting to a catheter with an ultrasound array. The ultrasonic system is operable for driving the ultrasound array. The method comprises the step of controlling the ultrasonic system to generate at least one acoustic radiation impulse with the ultrasonic system. The generated ultrasound energy is below a predetermined level.

The method further comprises the step of acquiring the magnetic resonance data by controlling the magnetic resonance imaging system with a pulse sequence at least partially during the generation of the at least one acoustic radiation impulse. The pulse sequence is an acoustic radiation force imaging pulse sequence. The method further comprises the step of reconstructing at least one acoustic radiation force pulse image using the magnetic resonance data. The method further comprises determining an energy deposition zone for the catheter using at least partially the at least one acoustic radiation force pulse image.

In another embodiment the method further comprises the step of determining a distance between the energy deposition zone and a predetermined volume in the subject.

In another aspect the invention provides for a computer program product comprising machine-executable instructions for execution by a processor controlling the medical apparatus. The medical apparatus comprises a magnetic resonance imaging system for acquiring magnetic resonance data from a subject. The medical apparatus further comprises an ultrasonic system operable for connecting to a catheter with an ultrasound array. The ultrasonic system is operable for driving the ultrasound array. Execution of the machine-executable instructions causes the processor to control the ultrasonic system to generate at least one acoustic radiation impulse with the ultrasonic system. The generated ultrasound energy is below a predetermined level.

Execution of the machine-executable instructions further cause the processor to acquire the magnetic resonance data by controlling the magnetic resonance imaging system with a pulse sequence at least partially during the generation of the at least one acoustic radiation impulse. The pulse sequence is an acoustic radiation force imaging pulse sequence. Execution of the machine-executable instructions further cause the processor to reconstruct at least one acoustic radiation force pulse image using the magnetic resonance data. Execution of the machine-executable instructions further cause the processor to determine an energy deposition zone for the catheter using at least partially the at least one acoustic radiation force pulse image.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
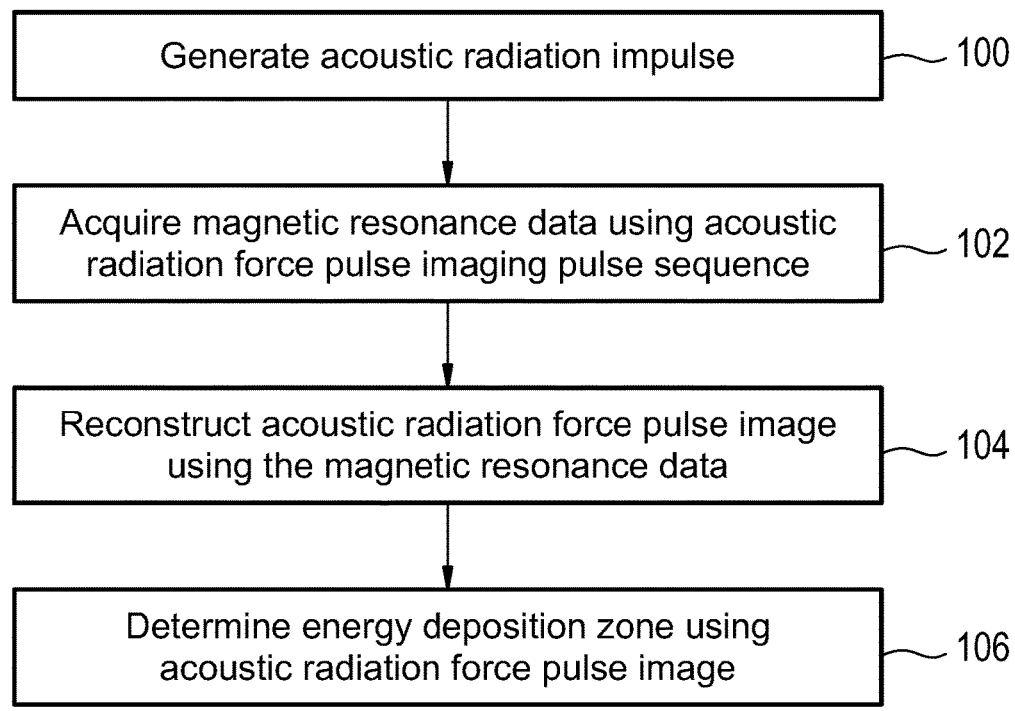
FIG. 1 shows a flow diagram which illustrates an example of a method.

FIG. 1 shows a flow diagram which illustrates a method according to an embodiment of the invention. In step 100 an acoustic radiation impulse is generated. This may be done using an ultrasonic system to control a catheter with an ultrasound array. Next in step 102 magnetic resonance data is acquired by controlling the magnetic resonance imaging system with a pulse sequence at least partially during the generation of the at least one acoustic radiation impulse. The pulse sequence is an acoustic radiation force imaging pulse sequence. Next in step 104 an acoustic radiation force pulse image is reconstructed using the magnetic resonance data. Finally in step 106 an energy deposition zone is determined using acoustic radiation force pulse image. By looking at the displacement of the subject's internal structure it can be determined where the majority of the energy deposition would be if for instance a sonication were performed.

Figure 2:
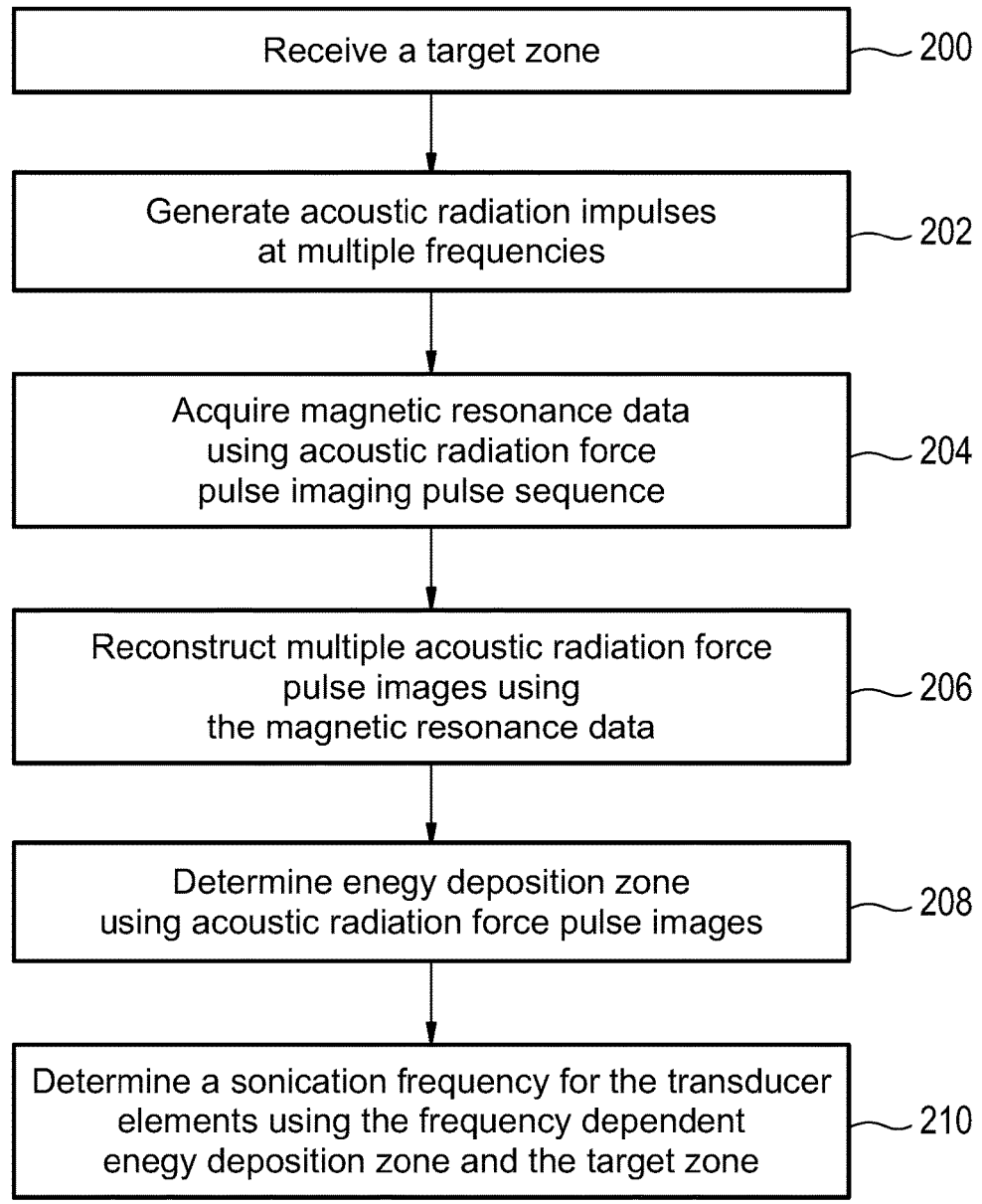
FIG. 2 shows a flow diagram which illustrates a further example of a method.

FIG. 2 shows a flow diagram which illustrates a further method according to an embodiment of the invention. First in step 200 a target zone is received. It may for instance be in the form of a treatment plan. The target zone is descriptive of a position in the internal anatomy of a subject which may be desired to be sonicated. Next in step 202 acoustic radiation impulses are generated at multiple frequencies. Next in step 204 magnetic resonance data is acquired using acoustic radiation force imaging pulse sequences and this is performed at least partially during the generation of the radiation pulses at multiple frequencies. Next in step 206 multiple acoustic radiation force pulse images are reconstructed using the magnetic resonance data. Next in step 208 the energy deposition zone is determined using the acoustic radiation force pulse images. Essentially this is a frequency-dependent energy deposition zone. When there are multiple transducers multiple frequencies may be used so that by controlling which transducers are used and/or which frequencies are used the location of the energy deposition zone can be controlled. Finally in step 210 a sonication frequency is determined for the transducer elements using the frequency-dependent energy deposition zone and the target zone. A frequency can be chosen for each of the transducer elements such that the energy deposition zone overlaps the target zone sufficiently well so that a sonication can be performed.

Figure 3:
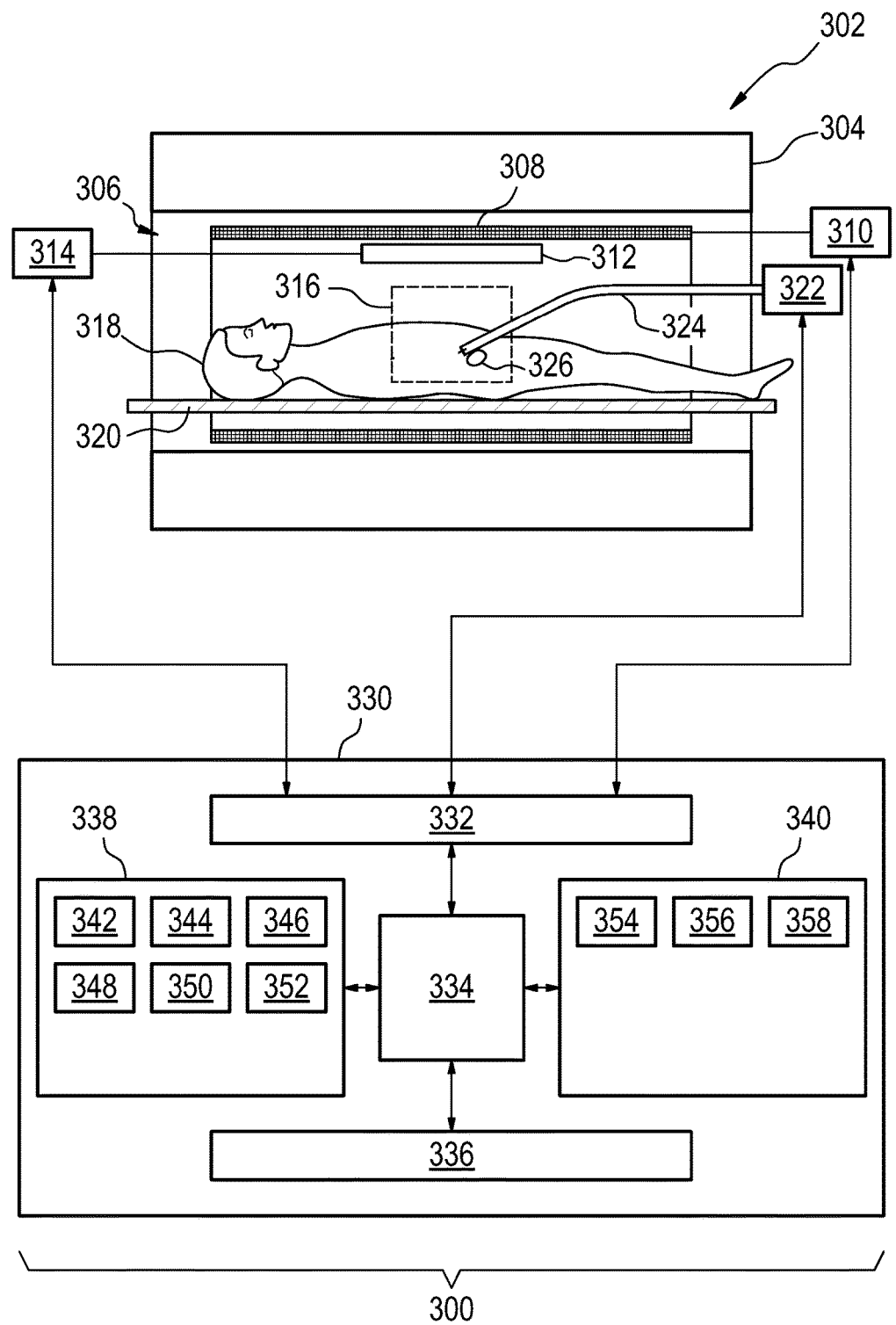
FIG. 3 shows a block diagram which illustrates an example of a medical apparatus.

FIG. 3 shows a medical apparatus 300 according to an embodiment of the invention. The magnetic resonance imaging system comprises a magnet 304. The magnet 304 is a cylindrical type superconducting magnet. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore of the cylindrical magnet there is an imaging zone where the magnetic field is strong and uniform enough to perform magnetic resonance imaging.

Within the bore 306 of the magnet 304 there is a magnetic field gradient coil 308 which is supplied current by a magnetic field gradient coil power supply 310. The magnetic field gradient coil 308 is used to spatially encode magnetic spins within an imaging zone of the magnet during the acquisition of magnetic resonance data. The magnetic field gradient coil 308 is intended to be representative. Typically magnetic field gradient coils contain three separate sets of coils for spatially encoding in three orthogonal spatial directions. The current supplied to the magnetic field coil 308 is controlled as a function of time and may be ramped or pulsed.

Within the bore of the magnet 306 is an imaging zone 316 where the magnetic field is uniform enough for performing magnetic resonance imaging. Adjacent to the imaging zone 316 is an antenna 312. The antenna 312 is connected to a transceiver 314. The radio frequency antenna 316 is for manipulating the orientations of magnetic spins within the imaging zone 316 and for receiving radio transmissions from spins also within the imaging zone. The radio frequency antenna may contain multiple coil elements. The radio frequency antenna may also be referred to as a channel. The radio frequency coil is connected to a radio frequency transceiver 314. The radio frequency coil 312 and radio frequency transceiver 314 may be replaced by separate transmit and receive coils and a separate transmitter and receiver. The radio frequency antenna is intended to also represent a dedicated transmit antenna and a dedicated receive antenna. Likewise the transceiver 314 may also represent a separate transmitter and receivers.

A subject 318 can be seen as reposing on the subject support 320. The subject is partially within the imaging zone. A catheter 324 is inserted into the subject 318. There is an energy deposition zone 326 which is shown as adjacent to the catheter 324. The catheter 324 is connected to an ultrasonic system 322 which provides electrical power for powering ultrasonic transducer arrays on the catheter 324. The energy deposition zone 326 is within the imaging zone 316.

The transceiver 314, the magnetic field gradient coil power supply 310, and the ultrasonic system 322 are shown as being connected to a hardware interface 332 of a computer system 330. The computer 330 also comprises a processor 334. The processor 334 is in communication with the hardware interface 332 which enables the processor 334 to control the operation and function of the medical apparatus 300. The processor 334 is also shown as being in communication with a user interface 336, computer storage 338, and computer memory 340.

The computer storage is shown as containing a treatment plan 342. The treatment plan 342 is a plan for sonicating a portion of the subject 318. It contains a target zone 344 which is descriptive of the anatomical position which may be desirous to sonicate. The computer storage 338 is shown as further containing a pulse sequence 346. The pulse sequence 346 contains a set of controls or commands which are executed in a time sequence which enables the magnetic resonance imaging system 302 to acquire magnetic resonance data using an acoustic radiation force imaging protocol. As such the pulse sequence 346 may also be used to control the ultrasound system 322. Computer storage 338 is further shown as containing magnetic resonance data 348 that was acquired using the pulse sequence 346. The computer storage 338 is further shown as containing acoustic radiation force pulse image that was reconstructed from the magnetic resonance data 348. The computer storage 338 is further shown as containing a location of the energy deposition zone 352 that was determined using the acoustic radiation force pulse image 350.

The computer memory 340 is further shown as containing a control module 354. The control module 354 contains computer-executable code which enables the processor 334 to control the operation and function of the medical apparatus 300. For instance it may enable the processor 334 to acquire the magnetic resonance data 348 using the pulse sequence 346. The computer memory 340 is further shown as containing an image reconstruction module 356. The image reconstruction module 356 contains computer-executable code which enables the processor 334 to reconstruct the acoustic radiation force pulse image 350 from the magnetic resonance data 348. The computer memory 340 further contains imaging processing module 358. The imaging processing module 358 contains computer-executable code which enables the processor 334 to determine the location of the energy deposition zone 352 from the acoustic radiation force pulse image 350.

Figure 4:
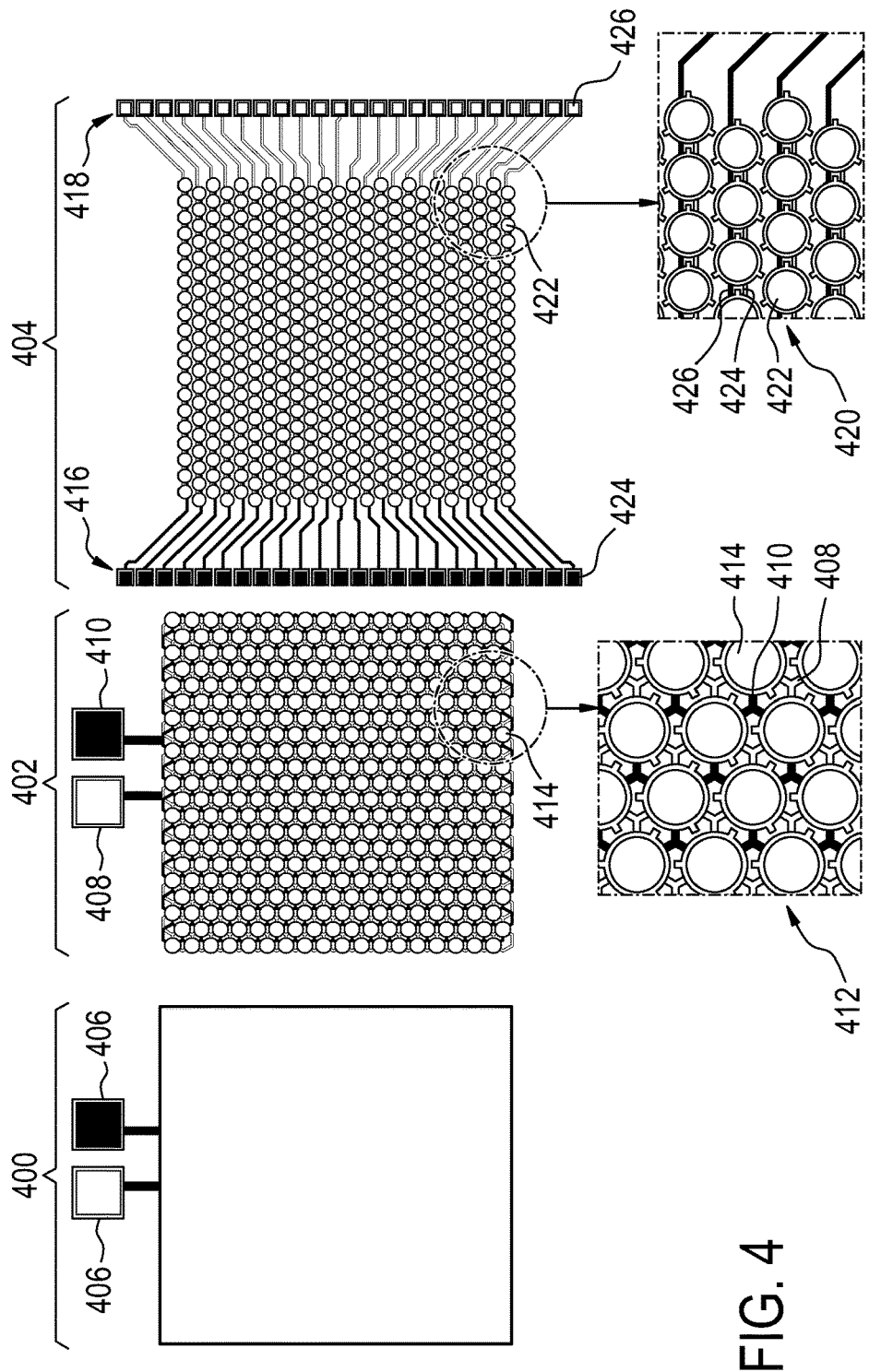
FIG. 4 illustrates several examples of ultrasound elements.

FIG. 4 shows several examples of transducer elements 400, 402, 404 that could be used in an embodiment. In FIG. 4 a conventional piezoelectric element 400 is shown. Next to the piezoelectric element 400 are two arrays 402, 404 of capacitive micromachined ultrasound transducers. The piezoelectric element 400 has two electrical connections 406 for driving the element 400.

The capacitive micromachined ultrasound transducer array 402 has first 408 and second 410 electrical connections. Array 402 is wired so that it functions as a single transducer element in the way that the piezoelectric element 400 does. This demonstrates how an array 402 may be used as a replacement for an entire piezoelectric element 400. Drawing 412 shows a blowup of array 402. The individual capacitive micromachined ultrasound transducers 414 can be seen. It can be seen that each of the transducers 414 is connected to the first 408 and second 410 electrical connections. The array 404 of capacitive micromachined ultrasound transducers is arranged as linear arrays. There is a set of first 416 and second 418 electrical connections for each row of transducers. Drawing 420 is a blowup detail of the array 404. An individual capacitive micromachined ultrasound transducer 422 can be shown as being connected to a first 424 and second 426 electrical connection. The connections 424 and 426 are chosen from the first 416 and second 418 sets of electrical connections.

In addition to wiring the capacitive micromachined ultrasound transducers in large block arrays or in linear arrays the individual micromachined ultrasound transducers may also be individually driven by their own source.

Figure 5:
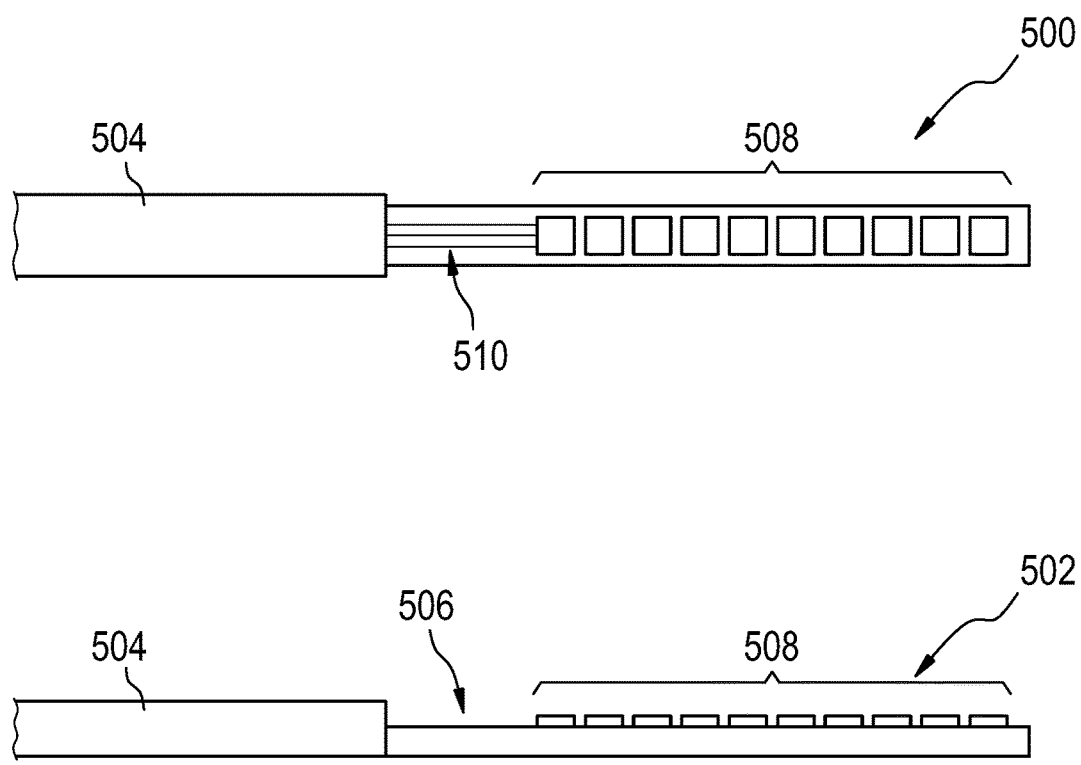
FIG. 5 illustrates an example of a catheter.

FIG. 5 shows a top view 500 and a side view 502 of a catheter 504. This is purely an example of one way in which a catheter could be built. There is the flat surface 506 upon which is mounted a number of ultrasound transducers 508. In this example the transducers are arranged as a linear array. There are electrical connections 510 which provide electrical power to each of the ultrasound transducers 508. The ultrasound transducers 508 could be piezoelectric transducers or they may even be individual arrays of CMUTs.

Figure 6:
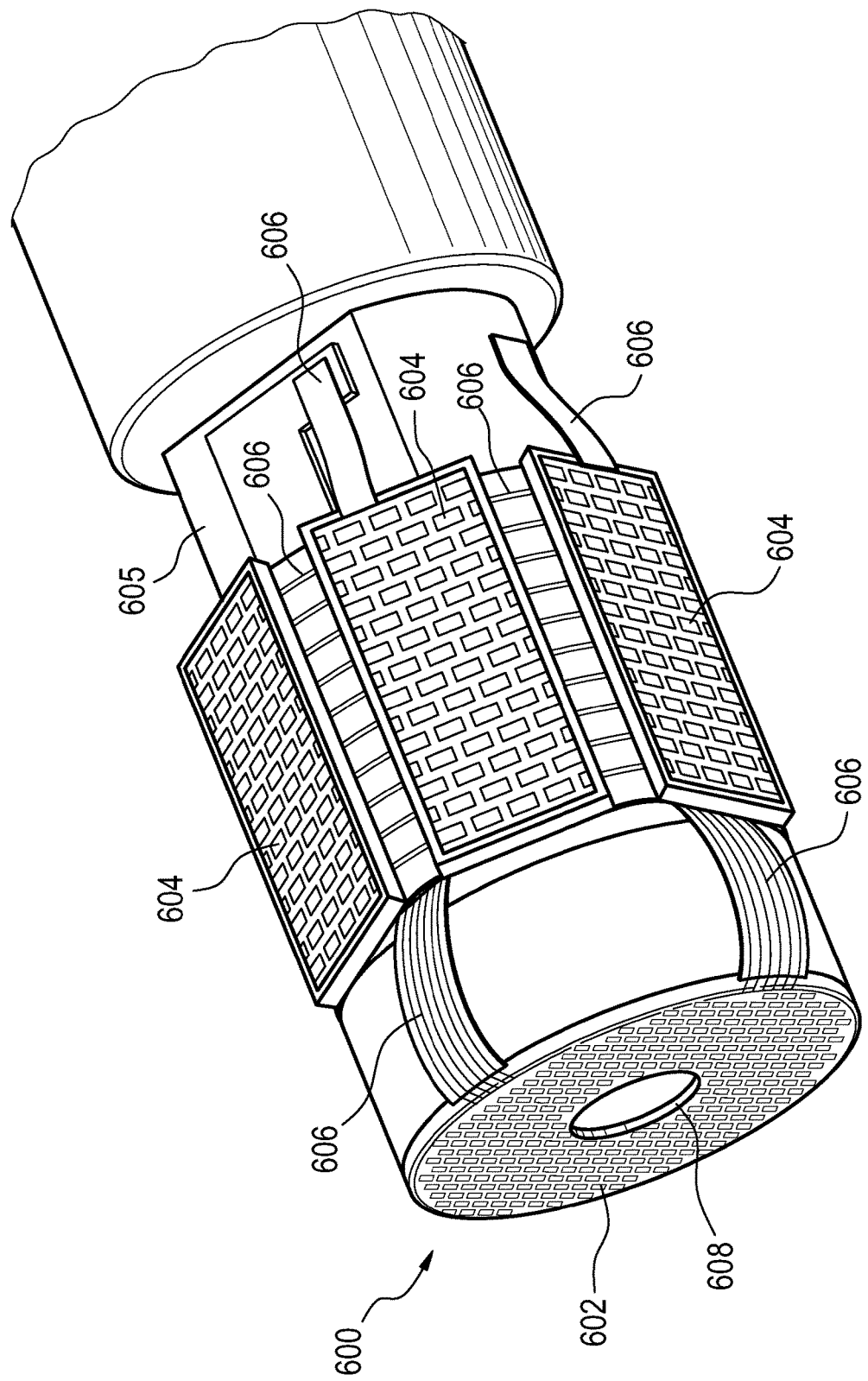
FIG. 6 illustrates a further example of a catheter.

FIG. 6 shows a distal end 600 of a catheter according to an embodiment of the invention. In this embodiment there is a forward-looking ring array 602. There is an array of capacitive micromachined ultrasound transducers surrounding a hole 608. Behind the ring array 602 are panels of sideways-looking arrays 604. The arrays 604 form a ring around the shaft of the catheter. Shown in this Fig. are various electrical connections 606. The forward-looking ring array 602 may be used for such things as providing three dimensional imaging. The sideways-looking arrays 604 may be used for ultrasound ablation and monitoring. The individual capacitive micromachined ultrasound transducers can be used for beam steering during ultrasound ablation. Benefits of this embodiment may include that there is no or minimal need for mechanically rotating the catheter. The hole 608 can be used for additional instruments or for water irrigation. The embodiment shown in FIG. 6 can focus in multiple directions so for such things as ablating a prostrate the entire 360 degrees around the probe may be performed simultaneously. This would result in less treatment time and thus also reduce costs.

Figure 7:
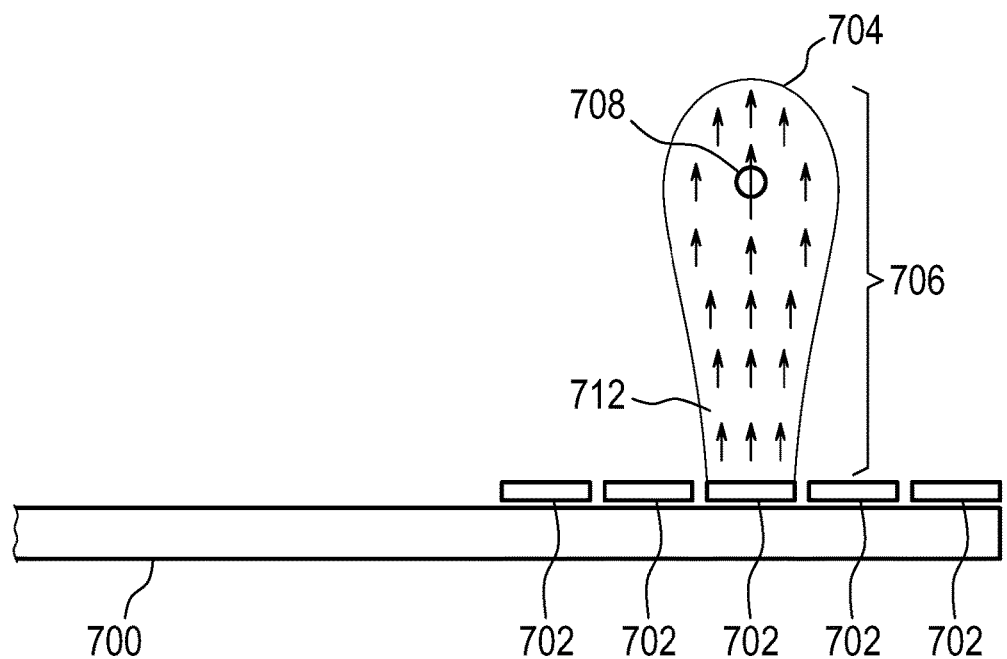
FIG. 7 illustrates a catheter to explain the functioning of a medical apparatus.

FIG. 7 is used to illustrate the functioning of a medical apparatus. Shown is a sketch of a catheter 700 with a number of transducer elements 702 mounted on the surface. For this example only the middle transducer element 702 is activated. The line 704 outlines the rough position of the radiation field from the ultrasound transducer 702. Within the ultrasound radiation field 704 magnetic resonance data has been acquired using an acoustic radiation force imaging protocol and the arrows 706 indicate a rough measure of displacement of tissue within the subject due to ultrasound. By looking at the magnitude of the arrow 706 it can be determined that the maximum deposition is at point 708. This may then be determined to be an energy deposition zone.

In addition to locating the maximum regions of the radiation field 704 can also be identified. For instance there is a beam path between the transducer element 702 and the maximum 708. Closer to the element 702 is the near field 712 of the ultrasound radiation field. In addition to just telling the maximum there is a large amount of information which will be descriptive of how the energy will be distributed to the subject by the transducer elements 702 when a sonication is performed. Such measurements can be performed for a single element, multiple elements, or even at different frequencies. For instance a map such as shown in FIG. 7 could be repeated for a variety of frequencies and this could be used then for accurately targeting ultrasound using the catheter 700.

Figure 8:
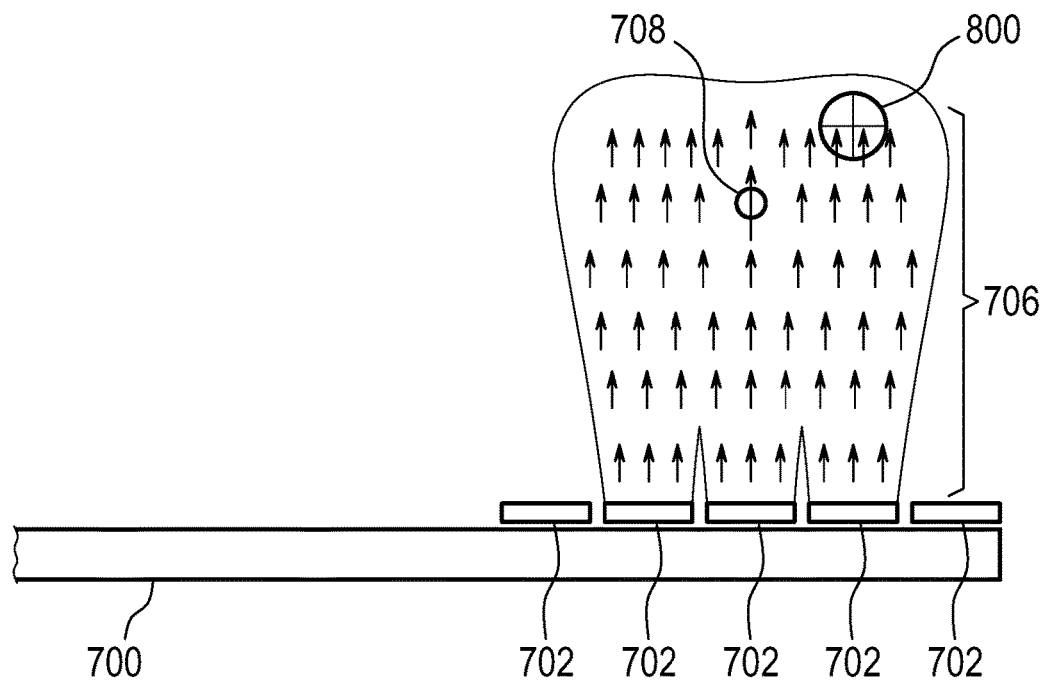
FIG. 8 illustrates a catheter to explain the further functioning of a medical apparatus.

FIG. 8 shows a further example of the catheter 700. In this example the ultrasound is generated by the three middle transducer elements 702. Again the energy deposition zone 708 can be seen. In addition a target zone 800 is marked on the diagram. This Fig. shows that the deposition zone 708 is not necessarily in the proper position for the target zone 800. Such a diagram could be displayed on the display of the medical instrument and can be used as a guide for a physician or other operator to position the catheter better or else also electronic steering techniques may be used, for instance different of the transducer elements 702 could be activated, or also the phase and/or frequency of the ultrasound generated could be changed such that the energy deposition zone 708 more closely matches the position of the target zone 800.

Acoustic radiation force imaging (ARFI) may be used for evaluating the acoustic environment and estimate the thermal damage that a sonication is likely to inflict without actually inducing any damage. This in turn allows for fine tuning the procedure before ablation that might further improve the safety and efficacy of the treatment.

HIFU therapy of prostate cancer is increasingly being used as a non-invasive alternative with the potential to reduce side effects such as impotence and incontinence, while still offering an efficient treatment. Most procedures to date have been made under ultrasound guidance. MR guidance offers several advantages such as temperature imaging, but also offers improvements during the planning stage.

One of the improvements that MRI offers is the potential to use acoustic radiation force imaging (ARFI) in the pre-planning step of these prostate cancer therapies. HIFU therapy of the prostate can be done either trans-rectal or sonicating through the rectal wall, or the HIFU device is transurethral and sonication occurs through the urethra wall. ARFI may in both cases be used with only minor total energy to ensure acoustic coupling from the HIFU device to the prostate. This is particularly a concern for trans-rectal HIFU as the rectal wall is very sensitive and may be damaged if the contact is poor, which would result in a local absorption of the HIFU energy potentially resulting in damaging of the rectal wall. This is less of a problem for the urethra, but will nevertheless hamper therapy if energy cannot be transmitted to where it should.

Often, HIFU therapy of prostate cancer is done as a whole gland therapy where the entire prostate is ablated. If the location of the cancer can be determined successfully within the prostate gland (a topic of active research in the MRI community) one can also do so called focal therapy where only the parts of the prostate thought to have cancer are treated. This is likely to reduce morbidity even further.

Another advantage given by ARFI, is that the pressure field can be estimated via the radiation force that the HIFU exerts on the tissue. The local pressure field is also the mechanisms via which the HIFU heats the tissue. Hence, an estimate of the distribution of the pressure field will give an idea of the distribution of the heating that may result. This can be used for improving the understanding of what is likely to happen close to sensitive structures such as the rectal wall, and in particular the nerve bundles (which are thought to control the penile functionality as well as bladder functionality). Moreover, if the transducer is capable of generating different frequencies the pressure fields of these different frequencies may be evaluated and compared using this ARFI method. This may aid in choosing the most appropriate frequency for the different parts of the prostate, thereby providing an even further improved safety.

Both piezo- and CMUT transducers can benefit from ARFI, although CMUTs can also have the benefit of optimizing the pressure field near the sensitive structures so that if cancer is found close to the nerve bundles (for example) the transducer angulation (CMUTs can be made mechanically steerable that is they can be controllably bent), frequency, and phase of the elements can be chosen so as for the pressure field to be high near the edge of the prostate but drop as fast as possible towards the sensitive nerve bundles.

ARFI of the prostate would allow for validating the acoustic path. For example, for a transurethral device (normally only around 10 elements whose individual pressure fields can be seen) one would expect to find some radiation force being exerted at the front face of each element. If not or there is a large difference between the elements, then there is likely an air pocket or similar within the urethra or catheter preventing the transducer element from performing as well as it could. This could damage the urethra (not such a big problem), damage the transducer, or lead to a suboptimal therapy if the problem is not seen and fixed. For the transrectal device, the benefits are outlined above.

The therapy planning would further be aided by allowing for a better understanding of the pressure field, and if the frequency can be changed then which frequency might be best suited to ablate which parts of the prostate. This is important for whole gland therapies as one would ideally like to fully ablate all of the prostate but nothing outside of the prostate (particularly not the nerve bundles). For focal therapy, one can analyse the different focal regions to be ablated separately.

All this can be done with ARFI at a fraction of the energy that would be needed for a test sonication. Also, ARFI can be done much more rapidly than a test sonication.

In one example, the sonication can be coupled with motion sensitizing gradients one can obtain a displacement image. Often, another image is needed with inverse motion sensitizing gradients in order to remove background information. These displacement values are dependent on the local radiation force, which are in turn dependent on the local pressure field.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

| | |
|---|---|
| 300 | medical apparatus |
| 302 | magnetic resonance imaging system |
| 304 | magnet |
| 306 | bore of magnet |
| 308 | magnetic field gradient coil |
| 310 | magnetic field gradient coil power supply |
| 312 | antenna |
| 314 | transceiver |
| 316 | imaging zone |
| 318 | subject |
| 320 | subject support |
| 322 | ultrasonic system |
| 324 | catheter |
| 326 | energy deposition zone |
| 330 | computer |
| 332 | hardware interface |
| 334 | processor |
| 336 | user interface |
| 338 | computer storage |
| 340 | computer memory |
| 342 | treatment plan |
| 344 | target zone |
| 346 | pulse sequence |
| 348 | magnetic resonance data |
| 350 | acoustic radiation force image |
| 352 | location of energy deposition zone |
| 354 | control module |
| 356 | image reconstruction module |
| 358 | image processing module |
| 400 | piezo element |
| 402 | array of capacitive micromachined ultrasound transducers |
| 404 | array of capacitive micromachined ultrasound transducers |
| 406 | electrical connections |
| 408 | first electrical connection |
| 410 | second electrical connection |
| 412 | blowup view of array 402 |
| 414 | capacitive micromachined ultrasound transducer |
| 416 | set of first electrical connections |
| 418 | set of second electrical connections |
| 420 | blowup view of array 404 |
| 422 | capacitive micromachined ultrasound transducer |
| 424 | first electrical connection |
| 426 | second electrical connection |
| 500 | top view |
| 502 | side view |
| 504 | catheter |
| 506 | flat surface |
| 508 | ultrasound transducers |
| 510 | electrical connections |
| 600 | distal end of catheter |
| 602 | forward looking ring array |
| 604 | sideward looking array |
| 605 | shaft |
| 606 | electrical connection |
| 608 | hole |
| 700 | catheter |
| 702 | transducer elements |
| 704 | ultrasound radiation field |
| 706 | displacement data |
| 708 | energy deposition zone |
| 710 | beam path |
| 712 | near field |
| 800 | target zone |

The invention claimed is:
1. A medical apparatus comprising:
  a magnetic resonance imaging system for acquiring magnetic resonance data from a subject;
  an ultrasonic system operable for connecting to a catheter with an ultrasound array, comprising multiple ultrasound elements, each of the multiple ultrasound elements being operable for producing ultrasound at multiple frequencies and wherein the ultrasonic system is operable for driving the ultrasound array;
  a memory for storing machine executable instructions;
  a processor for controlling the medical apparatus, wherein execution of the machine executable instructions cause the processor to:
    control the ultrasonic system to generate at least one acoustic radiation impulse with the ultrasonic system, wherein the generated ultrasound energy is below a predetermined level;
    acquire the magnetic resonance data by controlling the magnetic resonance imaging system with a pulse sequence at least partially during the generation of the at least one acoustic radiation impulse, wherein the pulse sequence is an acoustic radiation force imaging pulse sequence;
    reconstruct at least one acoustic radiation force pulse image using the magnetic resonance data; and
    determine an energy deposition zone for the catheter using at least partially the at least one acoustic radiation force pulse image and accurately target or direct the ultrasound array to deposit ultrasound energy into a target zone within the subject by controlling the phases of the ultrasound elements and, wherein the ultrasonic system is operable for controlling each of the ultrasound elements to generate ultrasound at the multiple frequencies, wherein the at least one acoustic radiation impulse comprises multiple impulses with ultrasound generated using at least some of the multiple frequencies, wherein execution of the instructions causes the processor to reconstruct multiple acoustic radiation force pulse images using magnetic resonance data acquired at least partially during the multiple pulses, wherein the execution of the machine executable instructions further cause the processor to receive a treatment plan descriptive of a target zone within the subject, and wherein the energy deposition zone is further determined at least partially using the multiple radiation force pulse images, and wherein execution of the instructions further cause the processor to to determine a sonication frequency for each of the ultrasound elements using the energy deposition zone as a function of frequency and the target zone.

2. The medical apparatus of claim 1, wherein the multiple ultrasound elements comprise at least one capacitive micromachined ultrasonic transducer array.

3. The medical apparatus of claim 2, wherein the ultrasonic system is operable for adjusting the focus of the at least one capacitive micromachined ultrasonic transducer array by controlling the phase of a electrical power supplied to capacitive elements of the at least one capacitive micromachined ultrasonic transducer, wherein execution of the machine executable instructions causes the processor to control the phase of electrical power supplied to capacitive elements of the at least one capacitive micromachined ultrasonic transducer to control the location of the energy deposition zone.

4. The medical apparatus of claim 1, wherein the multiple ultrasound elements comprise piezoelectric transducers.

5. The medical apparatus of claim 1, wherein the ultrasonic system is operable for controlling the phase of electrical power supplied to the ultrasound array, wherein execution of the machine executable instructions further causes the processor to adjust phase of multiple ultrasound transducer elements to modify the location of the energy deposition zone to match the target zone.

6. The medical apparatus of claim 1, wherein execution of the instructions causes the processor to control the ultrasonic system to generate ultrasound above the predetermined threshold in the energy deposition zone.

7. The medical apparatus of claim 1, wherein execution of the machine executable instructions further causes the processor to perform a beam path evaluation using the at least one acoustic radiation force pulse image.

8. The medical apparatus of claim 1, wherein execution of the machine executable instructions further causes the processor to determine a distance between the energy deposition zone and a predetermined volume in the subject.

9. The medical apparatus of claim 1, wherein the medical apparatus comprises the catheter.

10. The medical apparatus of claim 9, wherein the catheter is any one of the following: a transurethral catheter, interstitial catheter and an esophageal catheter.

11. A method of operating a medical apparatus, wherein the medical apparatus comprises a magnetic resonance imaging system for acquiring magnetic resonance data from a subject, wherein the medical apparatus further comprises an ultrasonic system operable for connecting to a catheter with an ultrasound array, comprising multiple ultrasound elements, each of the multiple ultrasound elements being operable for producing ultrasound at multiple frequencies and wherein the ultrasonic system is operable for driving the ultrasound array, wherein the method comprises the steps of:
controlling the ultrasonic system to generate at least one acoustic radiation impulse with the ultrasonic system, wherein the generated ultrasound energy is below a predetermined level;
acquiring the magnetic resonance data by controlling the magnetic resonance imaging system with a pulse sequence at least partially during the generation of the at least one acoustic radiation impulse, wherein the pulse sequence is an acoustic radiation force imaging pulse sequence;
reconstructing at least one acoustic radiation force pulse image using the magnetic resonance data; and
determining an energy deposition zone for the catheter using at least partially the at least one acoustic radiation force pulse image,
controlling each of the ultrasound elements to generate ultrasound at the multiple frequencies,
generate multiple impulses with ultrasound using at least some of the multiple frequencies, wherein execution of the instructions causes the processor to reconstruct multiple acoustic radiation force pulse images using magnetic resonance data acquired at least partially during the multiple pulses,
receive a treatment plan descriptive of a target zone within the subject, and wherein the energy deposition zone is further determined at least partially using the multiple radiation force pulse images, and
determine a sonication frequency for each of the ultrasound elements using the energy deposition zone as a function of frequency and the target zone.

12. The method of claim 11, wherein the method further comprises the step of determining a distance between the energy deposition zone and a predetermined volume in the subject.

13. A computer program product comprising machine executable instructions for execution by a processor controlling a medical apparatus, wherein the medical apparatus comprises a magnetic resonance imaging system for acquiring magnetic resonance data from a subject, wherein the medical apparatus further comprises an ultrasonic system operable for connecting to a catheter with an ultrasound array, comprising multiple ultrasound elements, each of the multiple ultrasound elements being operable for producing ultrasound at multiple frequencies and wherein the ultrasonic system is operable for driving the ultrasound array, wherein execution of the machine executable instructions cause the processor to:
control the ultrasonic system to generate at least one acoustic radiation impulse with the ultrasonic system, wherein the generated ultrasound energy is below a predetermined level;
acquire the magnetic resonance data by controlling the magnetic resonance imaging system with a pulse sequence at least partially during the generation of the at least one acoustic radiation impulse, wherein the pulse sequence is an acoustic radiation force imaging pulse sequence;
reconstruct at least one acoustic radiation force pulse image using the magnetic resonance data; and
determine an energy deposition zone for the catheter using at least partially the at least one acoustic radiation force pulse image
controlling each of the ultrasound elements to generate ultrasound at the multiple frequencies,
generate multiple impulses with ultrasound using at least some of the multiple frequencies, wherein execution of the instructions causes the processor to reconstruct multiple acoustic radiation force pulse images using magnetic resonance data acquired at least partially during the multiple pulses,
receive a treatment plan descriptive of a target zone within the subject, and wherein the energy deposition zone is further determined at least partially using the multiple radiation force pulse images, and
determine a sonication frequency for each of the ultrasound elements using the energy deposition zone as a function of frequency and the target zone.

* * * * *